(12) United States Patent
Kosa et al.

(10) Patent No.: US 10,871,484 B2
(45) Date of Patent: Dec. 22, 2020

(54) ENZYMATIC METHOD FOR DETECTING POLYAROMATIC HYDROCARBONS

(71) Applicant: BIOO Scientific Corporation, Austin, TX (US)

(72) Inventors: Nicolas M. Kosa, Austin, TX (US); Joseph F. Krebs, Austin, TX (US); Darshan N. Kasal, Fort Worth, TX (US)

(73) Assignee: BIOO Scientific Corporation, Austin, TX (US)

( * ) Notice: Subject to any disclaimer, the term of this patent is extended or adjusted under 35 U.S.C. 154(b) by 993 days.

(21) Appl. No.: 14/833,886

(22) Filed: Aug. 24, 2015

(65) Prior Publication Data

US 2016/0054230 A1     Feb. 25, 2016

Related U.S. Application Data

(60) Provisional application No. 62/040,819, filed on Aug. 22, 2014.

(51) Int. Cl.
    *C12Q 1/26*         (2006.01)
    *G01N 33/52*      (2006.01)

(52) U.S. Cl.
    CPC ............... *G01N 33/52* (2013.01); *C12Q 1/26* (2013.01); *G01N 2333/90241* (2013.01)

(58) Field of Classification Search
None
See application file for complete search history.

(56) References Cited

U.S. PATENT DOCUMENTS

| 9,127,301 | B2 | 9/2015 | Krebs et al. |
| 2014/0154723 | A1* | 6/2014 | Krebs ..................... C12Q 1/26 435/25 |

OTHER PUBLICATIONS

Chakraborty et al., Characterization of a Dihydrolipoyl Dehydrogenase Having Diaphorase Activity of Clostridium kluyveri, Bioscience, Biotechnology, and Biochemistry 72:4, 982-988 (2008).*
Hiada et al., 1-Methoxy-5-Methylphenazinium Methyl Sulfate, J. Biochem. 82, 1469-1473 (1977).*
Rampersad, Multiple Applications of Alamar Blue as an Indicator of Metabolic Function and Cellular Health in Cell Viablity Bioassays, Sensors 2012, 12, 12347-12360.*

* cited by examiner

*Primary Examiner* — Susan M Hanley
(74) *Attorney, Agent, or Firm* — Julie K. Staple; Dinsmore & Shohl LLP

(57) ABSTRACT

Polyaromatic hydrocarbons (PAH) from industrial waste and oil spills are a recurrent threat to food safety due to their stability and toxicity. Existing methods to establish the concentrations of PAH in environmental and food samples rely on expensive and laborious methodology. The teachings herein provide methods and kits for detecting the presence or absence of PAH. In certain embodiments, the quantity of PAH in a sample can be determined.

9 Claims, 7 Drawing Sheets

Tar in Sand, Triton X-114 Extraction and PAH Detection

| Spike, ppm | Dilution Factor | ΔAbs. 560 | Rxn Conc, ppm (NE*) | Sample Conc, ppm (NE*) | Spike Recovery, ppm (NE) |
|---|---|---|---|---|---|
| 0 | 196 | 0.261 | 1.0 | 189.8 |  |
| 100 | 196 | 0.335 | 1.5 | 297.2 | 107.4 |

*: "NE" = naphthalene equivalents. Assay response may vary with individual PAH, so PAH concentration is displayed as an equivalent absorbance to the naphthalene standard curve.

| Sample Spike Type | Sample Absorbance, 560 nm | Spike Extract/Expected Conc. (ppm) | Reported Conc. (ppm) | % Recovery |
|---|---|---|---|---|
| Fluorene | 0.278 | 8.3 | 6.1 | 74% |
|  | 0.179 | 4.2 | 3.3 | 80% |
| PAH Mix | 0.248 | 8.3 | 8.6 | 103% |
|  | 0.194 | 4.2 | 2.7 | 65% |

ENZYMATIC METHOD FOR DETECTING POLYAROMATIC HYDROCARBONS

CROSS-REFERENCE TO RELATED APPLICATIONS

This patent application claims a priority benefit under 35 U.S.C. § 119(e) from U.S. Provisional Patent Application No. 62/040,819 filed Aug. 22, 2014, which is incorporated herein by reference in its entirety.

STATEMENT REGARDING FEDERALLY SPONSORED RESEARCH

This work was performed in part with Government support under grant number 2R44FD004053-02 awarded by the U.S. Food and Drug Administration. The Government may have certain rights in the claimed inventions.

FIELD

The current teachings generally relate to methods and kits for determining the presence of polyaromatic hydrocarbons (PAH) in test samples, for example food or environmental samples. Some methods allow quantitation of PAH in a sample(s).

BACKGROUND

Oil spills are a recurrent threat to the environment and human health, with devastating long-lasting impacts for marine ecosystems and humans consuming tainted food. Spilled petroleum can rapidly spread due to ocean currents and winds to contaminate large areas. This is especially problematic for large spilled caused by offshore drilling or transportation incidents. Bioaccumulation of petroleum is especially pervasive in aquatic organism, including seafood, long after the original incident. Spilled petroleum and related compounds accumulate in sediment in the original impacted area, as well as spread by the contaminated species ingesting the material. Many species also do not efficiently metabolize the petroleum components which accumulate in their tissue, adding to the duration of spill repercussions.

Petroleum is comprised of a number of components posing human health threats, including alkanes, monoaromatic hydrocarbons, and polycyclic aromatic hydrocarbons (PAH). PAH represent a diverse range of structurally related molecules (FIG. 1). PAH are one of the most troublesome contaminants following an oil spill due to i) their high molecular weight/boiling point reduces "weathering" out of the aqueous marine environment compared to alkanes and monocyclic compounds ii) PAH are very slowly metabolized in animal life and iii) PAH can be very toxic and/or carcinogenic in animal life, including humans. Toxicity studies indicate that ingestion of PAH such as benzo[a]pyrene and naphthalene causes adverse health effects such as cancer, liver damage, birth defects, and reproductive harm. For these reasons, petroleum-adulterated food cannot be sold in the US, thereby disallowing harvest of seafood from areas affected by oil spills.

Testing is performed on seafood samples following oil spills in order to ensure contaminated seafood does not reach consumers, and to monitor petroleum contamination levels to deem affected areas safe after an incident. Three approved methods are currently implemented in measuring PAH contamination: gas chromatography mass spectrometry (GCMS), high performance liquid chromatography (HPLC), and sensory testing (organoleptic "taint" test). Existing methods for PAH analysis are expensive, require sophisticated instrumentation, and skilled operators. While organoleptic testing requires significantly less instrumentation than the alternatives, requiring analysis through an arguably subjective human sensory input limits test usefulness. Alternative methods such as immunological detection allows a limited ability to test certain single PAH compounds such as benzo[a]pyrene, it lacks the robustness to detect a wider variety of PAH for the purposes of a building a reliable broader detection method.

Enzyme-based assays are powerful tools for analytical testing. Enzymatic detection methods have broad reach in clinical applications for use in detecting DNA mutations, post-translational protein modification, and analyzing serum contents for glucose, lipids, and protein. In contrast to other analytical methods, enzymatic tests are typically rapid, specific, and robust. Unlike GCMS or HPLC, enzyme assays require less sophisticated instrumentation, tools, operators, and time to implement. Also, unlike HPLC and GCMS, enzymatic assays are compatible with surfactants, which are preferable in extracting organic compounds like PAH when hazardous organic solvents are impractical, prohibitively expensive, or environmentally unsafe to implement.

Microbial PAH dioxygenase enzymes are an interesting metabolic class of enzymes which evolved to degrade PAH in the environment and utilize them as a carbon source. Microbial dioxygenase are typically comprised of 3 components: an oxidase, a reductase, and a ferredoxin. Additionally, the enzyme requires an iron (II) cofactor ($Fe^{2+}$). The oxidase component binds molecular oxygen ($O_2$) and PAH, a reductase component which binds the oxidase and oxidizes NAD(P)H in concert with the oxygenation of PAH, and a ferredoxin which shuttles electrons between the reductase and oxidase. The oxidase itself is often comprised of a larger polypeptide subunit (alpha) and smaller polypeptide subunit (beta). A natural example of such an enzyme is naphthalene-1,2-dioxygenase (NDO) from *Pseudomonas putida*. The PAH is appended with two new alcohol/hydroxyl substituents following the reaction, and is termed a dihydroxy-dihydro PAH at this point.

While these enzymes are in principle well suited to chemical transformations pertaining to industrial applications like bioremediation, their multi-subunit structure and oxidation-sensitive iron cofactor contributes to instability and limits their usefulness outside a controlled environment.

Many downstream reactions occur to metabolize the modified PAH in microbes. A dehydrogenation reaction follows the initial PAH dioxygenase-facilitated oxygenation of a PAH. The dehydrogenation of the initial dihydroxy-dihydro PAH is catalyzed by a dihydroxy-dihydro PAH dehydrogenase. A natural example of such an enzyme is 1,2-dihydroxy-1,2-dihydronaphthalene dehydrogenase (NahB) from *Pseudomonas putida*. This enzyme is utilizes a $NAD(P)^+$ cofactor to dehydrogenate the dihydroxy-dihydro PAH to generate the diol PAH.

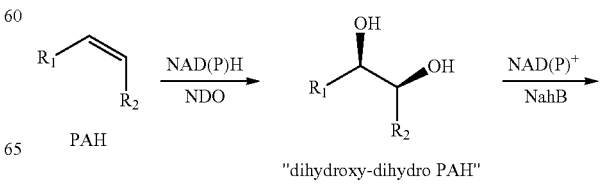

-continued

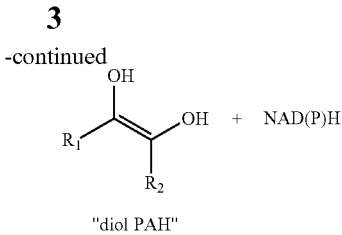

"diol PAH"

Existing FDA-approved methods for detecting PAH at legally defined concentration cutoffs are time-consuming, expensive, and require elaborate equipment. Fungal laccase and chemical reduction represented an early methodology to convert some PAH to a colorful "chromene" product. More recent enzymatic methods utilizing a three-enzyme one-pot reaction including bacterial PAH dioxygenase improved upon this methodology by eliminating the need for chemical reduction. This chromene can be a very colorful compound that may be detected by changes in absorbance at varying wavelengths. Unfortunately, the spectral characteristics of chromenes produced through reaction with various PAH are drastically different, leading to inconsistent detection of different PAH. A resulting core deficiency of these previous enzymatic methods is the inability to detect naphthalene, a core constituent of petroleum PAH and one of the more water-soluble PAH. It would be highly desirable to create a colorimetric enzyme assay capable of consistently detecting a broad variety of PAH.

SUMMARY

The current teachings provide various methods and kits for enzyme-mediated detection polyaromatic hydrocarbons (PAH). In certain embodiments, the PAH detection comprises qualitative analysis to determine if PAH is present or absent in the sample. In certain embodiments, the PAH detection comprises quantitative analysis to determine not only if PAH is present in the sample, but in what concentration. For example, by comparing the amount of detectable signal obtained from a test sample(s) with results obtained using known standards or standard curves created, for example, by serially diluting a control that contains a known concentration of PAH.

In certain embodiments, methods for detecting the presence of PAH in a sample are provided. In certain embodiments, methods for quantitating PAH in a sample are provided. According to certain disclosed methods, a sample that may or may not comprise at least one PAH, at least one PAH dioxygenase, and at least one NAD(P)H cofactor are combined to form a first reaction solution. The first reaction solution is incubated under conditions suitable for forming dihydroxy-dihydro PAH and NAD(P)$^+$. Next, at least one electron acceptor, at least one electron carrier, and at least one dihydroxy-dihydro PAH dehydrogenase to the first reaction solution to form a second reaction solution. The second reaction solution is incubated under conditions suitable for generating a detectable signal and the signal is measured to determine whether the sample contains PAH or not. In certain embodiments, the generated detectable signal is a colorimetric signal. In certain embodiments, the generated detectable signal is a fluorescent signal.

In certain embodiments, the first reaction composition further comprises at least one NAD(P)H deactivator. In certain embodiments, the at least one PAH dioxygenase and the at least one NAD(P)H deactivator are present in a recombinant cell lysate which is a component of the first reaction composition. In certain embodiments, the second reaction composition does not comprise an electron carrier.

Certain kit embodiments comprise at least one PAH dioxygenase, at least one NAD(P)H cofactor, at least one NAD(P)H deactivator, at least one dihydroxy-dihydro dehydrogenase, and at least one electron acceptor. Certain kit embodiments further comprise at least one electron carrier.

BRIEF DESCRIPTION OF THE FIGURES

The skilled artisan will understand that the figures, described below, are for illustration purposes only. The figures are not intended to limit the scope of the disclosed teachings in any way.

As seen in FIG. 4, all PAH species were detected using this exemplary method.

FIG. 5A—Detection of naphthalene standard in surfactant. A series of reaction solutions, each comprising NDO, NADH and varying amounts of naphthalene in 0.1% Triton X-114 in separate wells of a microtiter plate, were incubated for 30 minutes at room temperature. Next, 10 mM oxaloacetate was added to each of the reaction solutions and the microplate was incubated at room temperature for an additional 30 minutes. Next, Thiazoyl Blue Tetrazolium Bromide, MPMS, and NahB were added to each well, forming second reaction solutions. Detectable colorimetric signals were measured at 560 nm after a ten minute incubation. The results demonstrate that the signal intensity varied with the amount of naphthalene in the reaction solution. Samples from a petroleum tar and sand mixture cloud point extraction using Triton X-114 were analyzed to determine the PAH concentration. Two cloud point extract samples, one spiked with 100 ppm naphthalene, were combined with NDO and NAD(P)H in separate first reaction mixtures. These first reaction mixture were analyzed using the same exemplary method used to generate the naphthalene standard curve shown in FIG. 5A. The results, shown in FIG. 5B, demonstrate that the concentration of PAH in each of the cloud point extract samples could be determined using this exemplary method. The concentration of PAH in the spiked sample was determined to be slightly more than 100 PAH ppm greater than the unspiked sample, reflecting the additional 100 ppm of naphthalene that was added to that sample beforehand.

FIG. 7A—Fluorene and Environmental Protection Agency (EPA) Target Compound List (TCL) PAH Mix standards were prepared and analyzed with best-fit equations according to certain methods of the current teachings, using Thiazoyl Blue Tetrazolium Bromide as the detection chromophore. FIG. 7B—1 liter of aqueous samples comprising 1 ppm fluorene and 1 ppm TCL PAH Mix each were prepared and re-isolated using a solid phase extraction column. Eluates were diluted and evaluated, according to certain disclosed method embodiments, to quantify the concentration of PAH recovered from the extraction.

DETAILED DESCRIPTION OF CERTAIN EXEMPLARY EMBODIMENTS

Figure 1:
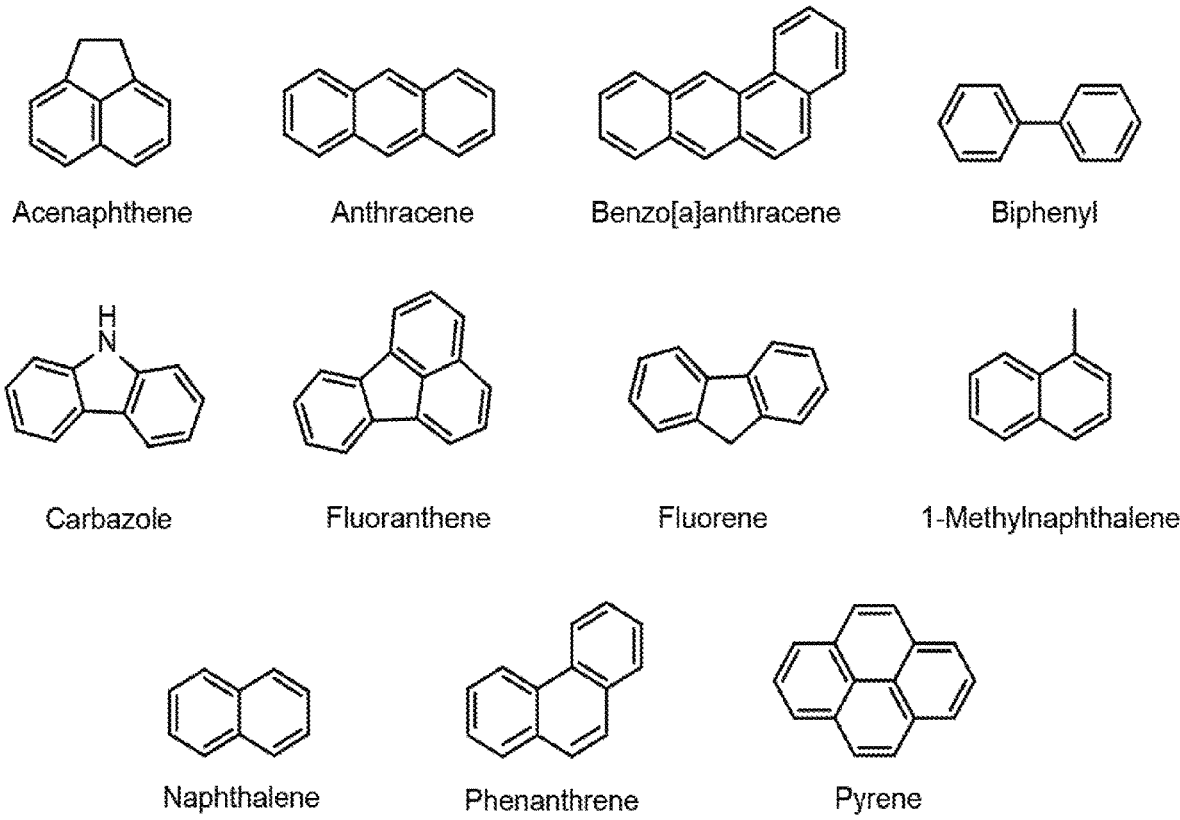
FIG. 1: PAH comprise a diversity of FDA-regulated compounds contained within petroleum and found in the vicinity of oil spills. These PAH consist of various mixtures of 5- and 6-membered aryl rings, and have various toxicities to wildlife and humans when consumed.
Figure 2A:
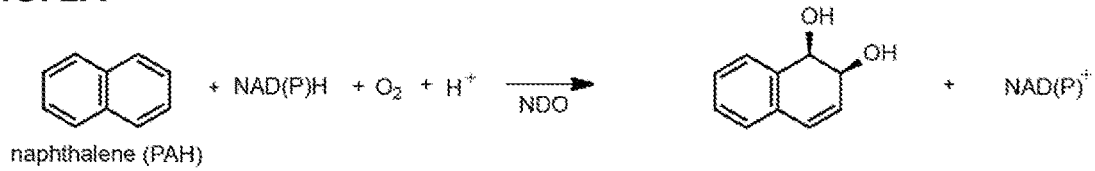
FIGS. 2A-2E: schematically depicts illustrative reaction steps that result from employing certain embodiments of the disclosed methods. A PAH such as naphthalene is converted by the PAH dioxygenase, naphthalene-1,2-dioxygenase (NDO) in this illustrative embodiment, in the presence of NAD(P)H, to its cis-dihydroxy-dihydro product and NAD(P)$^+$, depicted in FIG. 2A. Excess NAD(P)H is degraded to NAD(P)$^{30}$ by NAD(P)H deactivator, depicted in FIG. 2B. The dihydroxy-dihydro PAH product is subsequently converted by 1,2-dihydroxy-1,2-dihydronaphthalene dehydrogenase (NahB) in the presence of NAD(P)$^+$ to its dihydroxy derivative and NAD(P)H, depicted in FIG. 2C. To determine whether the sample comprises PAH, either a detectable colorimetric signal or a detectable fluorescent signal is generated (or not generated). An exemplary approach for generating a detectable colorimetric signal, depicted in FIG. 2D, comprises use of an electron acceptor, tetrazolium salt in this illustrative embodiment, and an electron carrier, 1-Methoxy-5-Methylphenazinium Methyl Sulfate (MPMS) in this illustrative embodiment. When tetrazolium salt and MPMS are added to the reaction solution, the tetrazolium is converted to the exemplary detectable colorimetric signal formazan. By measuring the detectable colorimetric signal, one is able to determine that the sample being tested comprised PAH. An exemplary approach for generating a detectable fluorescent signal, depicted in FIG. 2E, employs the electron acceptor diaphorase to reduce the non-fluorescent electron carrier resazurin into resorufin (an exemplary detectable fluorescent signal). In this exemplary embodiment, one can determine whether PAH was present in the sample by measuring the fluorescent signal.
Figure 2B:
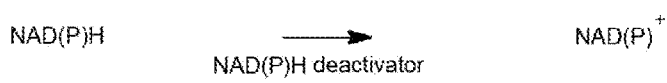
Figure 2C:
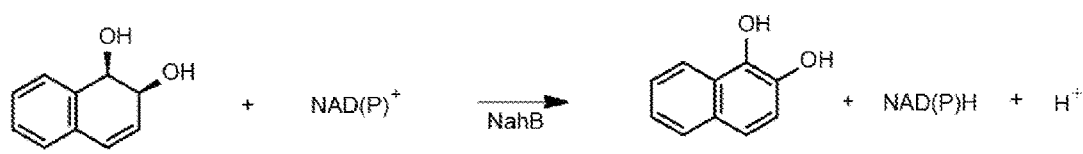
Figure 2D:
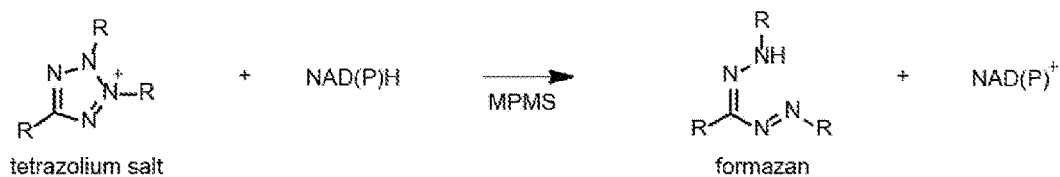
Figure 2E:
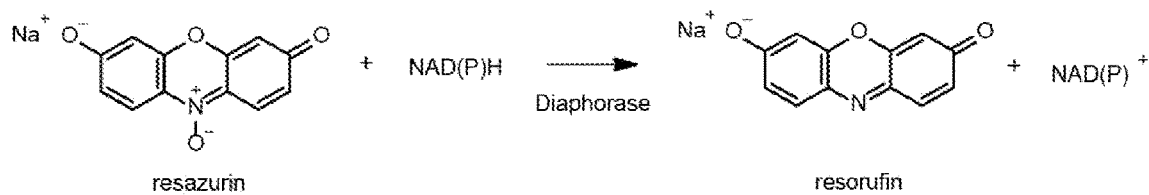
Figure 3:
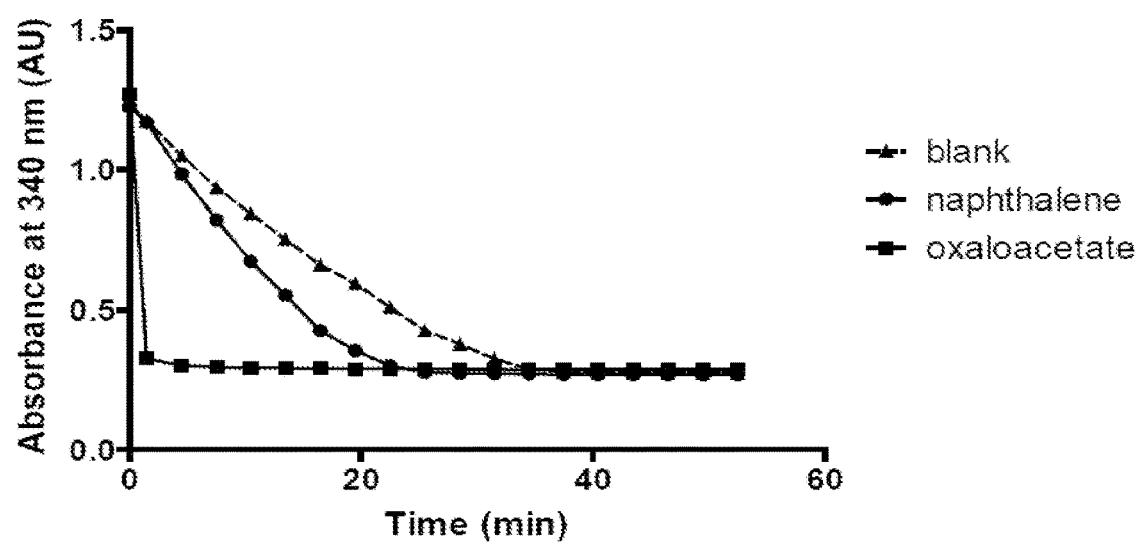
FIG. 3: Oxaloacetate-activated degradation of NADH with *E. coli* lysate comprising NDO. PAH-independent consumption of NADH can be increased by adding an accelerator, for example, oxaloacetate, to the reaction solution containing the *E. coli* lysate containing NDO, presumably due to the presence of bacterial metabolic enzymes in the *E. coli* lysate containing NDO. In this illustrative embodiment, oxaloacetate addition causes the consumption of NADH faster than addition of 20 ppm naphthalene. Acetonitrile is used as the diluent for naphthalene and was added to blank and oxaloacetate reaction solutions.

It is to be understood that both the foregoing general description and the following detailed descriptions are illustrative and exemplary only and are not intended to limit the scope of the disclosed teachings. The section headings used herein are for organizational purposes only and are not to be construed as limiting the subject matter of the disclosed teachings.

Definitions

The abbreviations used herein have their conventional meaning within the chemical and biological arts. The chemical structures and formulae set forth herein are constructed according to the standard rule of chemical valency known in the chemical arts.

Where substituent groups are specified by their conventional chemical formulae, written from left to right, they equally encompass the chemically identical substituents that would result from writing the structure from right to left, e.g., —CH2— is equivalent to —OCH2—.

The term "aryl" means, unless otherwise stated, a polyunsaturated, aromatic, hydrocarbon chemical, which can be a single ring or multiple rings (e.g. 2 to 10 rings) that are fused together (i.e., a fused ring aryl) or linked covalently. This aryl compound may either be covalently unattached, or attached to non-aryl chemical groups.

The term "NAD(P)H" means, unless otherwise stated, the unphosphorylated reduced nicotinamide adenine dinucleotide "NADH", the phosphorylated reduced nicotinamide adenine dinucleotide phosphate "NADPH", as well as the thio derivative, thio-NAD(P)H. Likewise, The term "NAD(P)$^+$" means, unless otherwise stated, the unphosphorylated oxidized nicotinamide adenine dinucleotide "NAD$^+$", the oxidized nicotinamide adenine dinucleotide phosphate "NADP$^+$" and the thio derivative, thio-NAD(P)$^+$.

As used herein, "expression vector" refers to polynucleotide elements that are used to introduce recombinant nucleic acid into cells for either expression or replication.

The terms "identity" and "percent identity," in the context of two or more polypeptide or polynucleotide sequences, refers to two or more sequences or subsequences that are the same or have a specified percentage of amino acid residues or nucleic acids that are the same (e.g. share at least about 50%, at least about 70%, at least about 90%, at least about 95%, at least about 99% identity) over a specified region to a reference sequence, when compared and aligned for maximum correspondence over a comparison window using a sequence comparison algorithm or by manual alignment and visual inspection.

Optimal alignment of sequences for comparison and determination of sequence identity can be determined by a sequence comparison algorithm or by visual inspection. When optimally aligning sequences and determining sequence identity by visual inspection, percent sequence identity is calculated as the number of residues of the test sequence that are identical to the reference sequence divided by the number of non-gap positions, multiplied by 100. When using a sequence comparison algorithm, test and reference sequences are entered into a computer program, subsequence coordinates and sequence algorithm program parameters are designated. The sequence comparison algorithm then calculates the percent sequence identities for the test sequences relative to the reference sequence based on the program parameters as known in the art. For example BLAST or BLAST 2.0. Alignment can be carried out for sequences containing deletions and/or additions, substitutions, polymorphisms, and man-made variants.

Exemplary Reagents

Various embodiments of the disclosed methods and kits typically comprise at least one PAH dioxygenase, at least one NAD(P)H cofactor, at least one NAD(P)H deactivator, at least one dihydroxy-dihydro PAH dehydrogenase, and at least one electron acceptor. Certain embodiments, the disclosed methods and kits further comprise at least one electron carrier. Certain embodiments of the disclosed methods and kits further comprise at least one chromophore, at least one fluorophore, or both.

Exemplary PAH dioxygenases include: NDO, for example, NDO from *Pseudomonas putida*; biphenyl 2,3-dioxygenase, for example, biphenyl-2,3-dioxygenase from *Pseudomonas* sp., *Rhodococcus* sp., *Comamonas testosterone*, or *Burkholderia xenovorans*; benzene-1,2-dioxygenase, for example, benzene-1,2-dioxygenase from *Pseudomonas* sp.; carbazole 1,9a-dioxygenase, for example, carbazole 1,9a-dioxygenase may be from *Pseudomonas* sp. It is to be understood that the same or similar PAH dioxygenases may be obtained from other organisms, or synthesized chemically or biochemically (for example but not limited to, recombinant expression or in vitro transcription and translation), and that such PAH dioxygenases are within the scope of the current teachings. In certain embodiments, the PAH dioxygenase has at least 60, 70, 80, 90, 95, 96, 97, 98, 99, or 100% sequence homology to a wild type (i.e., naturally occurring) PAH dioxygenase.

Exemplary NAD(P)H Cofactors Include NADPH, NADH, and Thio-NADH

Exemplary dihydroxy-dihydro PAH dehydrogenases include: 1,2-dihydroxy-1,2-dihydronaphthalene dehydrogenase, for example, from *Pseudomonas putida*; and cis-3,4-dihydrophenanthrene-3,4-diol dehydrogenase, for example, from *Alcaligenes faecalis* or *Comamonas testosteroni*. It is to be understood that the same or similar dihydroxy-dihydro dehydrogenases may be obtained from other organisms, or synthesized chemically or biochemically (for example but not limited to, recombinant expression or in vitro transcription and translation), and that such dihydroxy-dihydro PAH dehydrogenases are within the scope of the current teachings. In certain embodiments, the dihydroxy-dihydro PAH dehydrogenase has at least 60, 70, 80, 90, 95, 96, 97, 98, 99, or 100% sequence homology to a wild type dihydroxy-dihydro PAH dehydrogenase.

In certain embodiments, an electron acceptor comprises a detectable moiety or a reactive chemical. In certain embodiments, the detectable moiety may be a chromophore. For example, a chromophore may have higher visible absorbance in its reduced state. Exemplary chromophores for use in the disclosed methods and kits are tetrazolium salts. Non-limiting examples of tetrazolium salts include Thiazoyl Blue Tetrazolium Bromide (MTT), 2-(4-iodophenyl)-3-(4-nitrophenyl)-5-phenyl-2H-tetrazolium (INT), water soluble tetrazolium 1 (WST-1), and tetranitroblue tetrazolium chloride (TNBT). In certain embodiments, the detectable moiety is a fluorophore, such as a fluorophore in an oxidized or reduced state. For example, resazurin (oxidized state, non-fluorescent) and resorufin (reduced state, fluorescent).

In certain embodiments, the conversion of NAD(P)H to NAD(P)$^+$ and a detectable signal is facilitated by an electron carrier. In certain embodiments, the electron carrier comprises a chemical, for example a phenazinium methyl sulfate derivative, such as 1-Methoxy-5-Methylphenazinium Methyl Sulfate (MPMS) or phenazine methosulfate. In certain embodiments, the electron carrier comprises an enzyme, for example, a diaphorase. Exemplary diaphorases include: dihydrolipoyl dehydrogenase from *Clostridium kluyveri*; ferredoxin reductase from *Spinacia oleracea* or *Bacillus subtilis*; and NADH oxidase from *Streptococcus mutans*. It is to be understood that the same or similar diaphorases may be obtained from other organisms, or synthesized chemically or biochemically (for example but not limited to, recombinant expression or in vitro transcription and translation), and that such diaphorases are within the scope of the current teachings. In certain embodiments, the diaphorase has at least 60, 70, 80, 90, 95, 96, 97, 98, 99, or 100% sequence homology to a wild type diaphorase.

In certain embodiments, recombinant cell lysates (including clarified supernatants) comprising the at least one PAH dioxygenase, the at least one NAD(P)H deactivator, the at least one PAH dihydroxy-dihydro dehydrogenase, or combinations, may be employed.

PAH dioxygenase preparation. Naphthalene dioxygenase (NDO) from *Pseudomonas putida* was expressed in *E. coli* strain BL-21 (DE3) with the transformed plasmid pDTG141 encoding the genes for all four enzyme subunits. RI medium is prepared by dissolving 20 g tryptone, 10 g yeast extract, 5 g sodium chloride in 1 L ddH$_2$O, and adjusting pH of solution to 7.4 with sodium hydroxide. These cells were grown in RI medium with 25 µg/mL ampicillin at 30° C. with rotary shaking in baffled flasks at 300 rpm. When the cultures reached an OD of 0.8 at 600 nm, IPTG was added to a final concentration of 0.2 mM in the culture media. Cultures were then incubated with shaking overnight at 16° C. Centrifugation of overnight cultures at 3000 rpm for 30 minutes at 4° C. produced a cell pellet, which was stored at −20° C. for typically no longer than 3 months until lysis. Cell pellet from 1 liter of NDO culture proceeded with re-suspension of cell pellet in 50 mL of NDO lysis buffer (50 mM TrisCl pH 7.0, 5% glycerol, 1 mM DTT, 0.1 mg/mL lysozyme (from chicken egg white), 4 µL Benzonase nuclease (Sigma). Occasional shaking of culture on ice effected sufficient lysis over a 20 minute period. Soluble supernatant was separated from insoluble fraction with centrifugation at 10,000 rpm at 4° C. for 45 minutes. Soluble lysate was dialyzed twice against NDO lysis buffer without lysozyme/Benzonase for 4-8 hours each at 4° C. NDO was aliquoted and stored at −80° C. until further use.

PAH dihydroxy-dihydro dehydrogenase preparation. 1,2-dihydroxy-1,2-dihydronaphthalene dehydrogenase (NahB) from *Pseudomonas putida* was expressed in *E. coli* strain BL-21 Star (DE3) with the transformed plasmid pET24b. These cells were grown in RI medium with 50 µg/mL kanamycin sulfate at 37° C. with rotary shaking in baffled flasks at 300 rpm. When the cultures reached an OD of 2 at 600 nm, IPTG was added to a final concentration of 0.2 mM. Cultures were then incubated with shaking overnight at 18° C. Centrifugation of overnight cultures at 3000 rpm for 30 minutes at 4° C. produced a cell pellet, which was stored at −20° C. until lysis. Cell pellet from 1 liter of NahB culture proceeded with re-suspension of cell pellet in 50 mL of NahB lysis buffer (20 mM potassium phosphate pH 7.2, 10% ethanol, 0.5 mM DTT). Resuspended cells were lysed with passage through a microfluidizer. Soluble supernatant was separated from insoluble fraction with centrifugation at 10,000 rpm at 4° C. for 45 minutes. Lysate supernatants comprising NahB was aliquoted and stored at −80° C. until further use.

PAH dihydroxy-dihydro dehydrogenase purification. Lysate supernatants comprising NahB was thawed from storage at −80° C. on ice, and filtered with a 0.2 µm cellulose acetate syringe filter. A Pharmacia XK-16 FPLC column containing 30 mL bed-volume of GE Q Sepharose Fast Flow resin was prepared for use with a 0 M NaCl and 1 M NaCl mobile phases in 20 mM sodium phosphate pH 7.2, 10% ethanol, 0.5 mM DTT at 4° C. A FPLC program established for a flow rate of 5 mL/min. 10 mL of NahB was loaded with 0 M NaCl mobile phase, washed for 20 minutes with 0 M NaCl mobile phase and subjected to a gradient resulting in 0.3 M NaCl after 30 minutes. The gradient increased to result in a 1 M NaCl concentration after 10 minutes, and was held for an additional 10 minutes at 1 M NaCl. The column was then washed for 10 minutes with 0 M NaCl mobile phase for regeneration. NahB FPLC fractions containing over 90% pure protein by SDS-PAGE were combined, and dialyzed against 20 mM sodium phosphate pH 7.2 overnight at 4° C. Dialyzed protein was concentrated to 360 µM with centrifugal filtration using 10 kDa molecular weight cutoff (MWCO) filters at 4° C., and added to an equal volume of glycerol to generate a final stock of 180 µM for storage at −20° C. According to certain method embodiments, the PAH dihydroxy-dihydro dehydrogenase comprises at least one of: recombinant cell lysate comprising NahB or another PAH dihydroxy-dihydro dehydrogenase activity, a clarified supernatant from such lysates, semi-purified enzyme, for example FPLC purified NahB, or purified NahB or another PAH dihydroxy-dihydro dehydrogenase.

Exemplary Methods

In certain embodiments, methods for generating a detectable signal in the presence of PAH are provided. According to certain disclosed methods, a sample that may or may not comprise at least one PAH, at least one PAH dioxygenase, and at least one NAD(P)H cofactor are combined to form a first reaction solution. The first reaction solution is incubated under conditions suitable for allowing the PAH dioxygenase to convert the PAH to its dihydroxy-dihydro derivative and depletion of NAD(P)H cofactor. Next, at least one electron acceptor, at least one electron carrier, and at least one dihydroxy-dihydro PAH dehydrogenase to the first reaction solution to form a second reaction solution. The second reaction solution is incubated under conditions suitable for generating a detectable signal and the signal is measured to determine whether the sample contains PAH or not. In certain embodiments, the generated detectable signal is a colorimetric signal. In certain embodiments, the generated detectable signal is a fluorescent signal.

In certain embodiments, a recombinant cell lysate comprising at least one PAH dioxygenase and at least one NAD(P)H deactivator is combined with a sample to form a first reaction composition. In certain embodiments, the activity of the NAD(P)H deactivator is enhanced by the presence of an accelerator, for example oxaloacetate or oxaloacetic acid.

In certain embodiments, NAD(P)+ is converted to NAD(P)H by the dihydroxy-dihydro PAH dehydrogenase in the presence of dihydroxy-dihydro PAH. In certain embodiments, NAD(P)H produced by dihydroxy-dihydro PAH dehydrogenase reacts with the electron acceptor to generate NAD(P)+ and a detectable signal.

In certain embodiments, the at least one PAH dioxygenase comprises at least one of: naphthalene-1,2-dioxygenase, for example, naphthalene-1,2-dioxygenase from *Pseudomonas putida*; biphenyl 2,3-dioxygenase, for example, biphenyl-2,3-dioxygenase from *Pseudomonas* sp., *Rhodococcus* sp., *Comamonas testosterone*, or *Burkholderia xenovorans*; benzene-1,2-dioxygenase, for example, benzene-1,2-dioxygenase from *Pseudomonas* sp.; carbazole 1,9a-dioxygenase, for example, carbazole 1,9a-dioxygenase may be from *Pseudomonas* sp.

In certain embodiments, the at least one dihydroxy-dihydro PAH dehydrogenases include: 1,2-dihydroxy-1,2-dihydronaphthalene dehydrogenase (, for example, from *Pseudomonas putida*; and cis-3,4-dihydrophenanthrene-3,4-diol dehydrogenase, for example, from *Alcaligenes faecalis* or *Comamonas testosteroni*.

In certain embodiments, the at least one electron acceptor comprises at least one of: resazurin and tetrazolium salts, for example, Thiazoyl Blue Tetrazolium Bromide (MTT), 2-(4-iodophenyl)-3-(4-nitrophenyl)-5-phenyl-2H-tetrazolium (INT), water soluble tetrazolium 1 (WST-1), or tetranitroblue tetrazolium chloride (TNBT)

In certain embodiments, the at least one electron carrier comprises at least one phenazinium methyl sulfate derivative, for example, at least one of: 1-Methoxy-5-Methylphenazinium Methyl Sulfate (MPMS) or phenazine methosulfate; at least one diaphorase, for example, at least one of: dihydrolipoyl dehydrogenase from *Clostridium kluyveri*; ferredoxin reductase from *Spinacia oleracea* or *Bacillus subtilis*; and NADH oxidase from *Streptococcus mutans*.

In certain embodiments, the PAH is extracted from its original source, for example, by using an organic solvent, such as acetonitrile, or water and surfactant(s). Exemplary surfactants include Triton X-114, Triton X-100, Tween-20, Tween-80, octyl-beta glucoside, sodium cholate, Turgitol® 15-S-7, or Turgitol® 15-S-9. In certain embodiments, the extracted PAH is concentrated. The extraction method may use a solid phase sorbant. The solid phase sorbant may be C18 silica. The solid phase sorbant may be contained in a column. The column may be a GracePure™ SPE C18-Max. The column may be a Phenomenex Strata PAH 8B-S130-WCH. The solid phase sorbant may be contained in a filter disk. The filter disk may be a 3M Empore™ #2215-C18 extraction disk. The PAH may be eluted from the column with an organic solvent.

In certain embodiments, the addition of either reduced nicotinamide adenine dinucleotide (NADH) or reduced nicotinamide adenine dinucleotide phosphate (NADPH) elicits enzyme activities. The enzyme compatibility allows an interchangeable nature of the nicotinamide substrate, thus allowing reference to either or both substrate as NAD(P)H.

In certain embodiments, active NAD(P)H deactivator present in enzyme reactions reacts with residual NAD(P)H at a rate slower than the reactions of PAH dioxygenase with PAH and electron acceptor with NAD(P)H. According to certain disclosed methods, the NAD(P)H deactivator converts NAD(P)H to NAD(P)+ in a PAH-independent manner. In certain method and kit embodiments, the NAD(P)H deactivator may be contained in a *P. putida* PAH dioxygenase heterologous expression from *E. coli* BL-21(DE3) or JM109 (DE3) cell lysate. Typically such lysates comprise both PAH dioxygenase and NAD(P)H deactivator activity. In certain embodiments, the NAD(P)H deactivator is accelerated by an NAD(P)H deactivator accelerator, for example, oxaloacetate or oxaloacetic acid.

In certain embodiments, an electron carrier facilitates the conversion of an oxidized electron acceptor to its reduced form in the presence of NAD(P)H. The reduction of electron acceptor occurs in a manner proportional to the NAD(P)H produced.

In certain method embodiments, NAD(P)H mediates the reduction of an electron acceptor to generate an observed signal. The level of signal generated is proportional to the amount of NAD(P)H produced.

Exemplary Kits

In certain embodiments, kits are provided to expedite the performance of various disclosed methods. Kits serve to expedite the performance of certain method embodiments by assembling two or more reagents and/or components used in carrying out certain methods. Kits may contain reagents in pre-measured unit amounts to minimize the need for measurements by end-users. Kit may also include instructions for performing one or more of the disclosed methods. In certain embodiments, at least some of the kit components are optimized to perform in conjunction with each other. Typically, kit reagents may be provided in solid, liquid, or gel form.

In certain embodiments, kits for determining the presence of PAH are provided. In certain embodiments, kits comprise at least one PAH dioxygenase, at least one NAD(P)H cofactor, at least one NAD(P)H deactivator, at least one dihydroxy-dihydro PAH dehydrogenase, and at least one electron acceptor.

In certain embodiments, kits for detecting PAH comprise at least one PAH dioxygenase enzyme, at least one dihydroxy-dihydro PAH dehydrogenase, at least one electron acceptor, at least one NAD(P)H cofactor, and at least one NAD(P)H deactivator.

Certain method and kit embodiments comprise at least one NAD(P)H cofactor, at least one NAD(P)H deactivator, at least one dihydroxy-dihydro PAH dehydrogenase, at least one electron acceptor, and at least one recombinant expression cell lysate comprising at least one PAH dioxygenase and NAD(P)H deactivator activity.

Certain kit embodiments comprise at least one recombinant vector capable of expressing at least one PAH dehydrogenase and at least one NAD(P)H deactivator activity. Certain kit embodiments comprise at least one recombinant vector capable of expressing at least one PAH dehydrogenase. Certain kit embodiments comprise at least one recombinant vector capable of expressing at least one NAD(P)H deactivator activity.

Certain kit embodiments comprise at least one electron carrier, for example, at least one phenazinium methyl sulfate derivative, at least one diaphorase, or both. Certain kit embodiments comprise at least one accelerator, for example, oxaloacetate.

Certain kit embodiments comprise a PAH standard reagent, for example, to allow the end-user to readily create a standard curve or for use as a positive control. Exemplary PAH standard reagents comprise Acenaphthene, Anthracene, Benzo[a]anthracene, Biphenyl, Carbazole, Fluoranthene, Fluorene, 1-Methylnaphthalene, Naphthalene, Phenanthrene, or Pyrene.

Certain kit embodiments comprise at least one NAD(P)H deactivator accelerator, for example, oxaloacetate or oxaloacetic acid.

Certain kit embodiments comprise at least one extraction component. In certain embodiments, the extraction component comprises an organic solvent, for example, acetonitrile, dimethyl formamide, dimethyl sulfoxide, dichloromethane, isopropanol, ethanol, or methanol. The organic solvent may be dissolved in water. In certain embodiments, the extraction component comprises an aqueous solvent. In certain embodiments, the aqueous solvent comprises at least one surfactant. In certain embodiments, the surfactant comprises at least one of: Triton X-114, Triton X-100, Tween-20, Tween-80, octyl-beta glucoside, sodium cholate, Turgitol® 15-S-7, or Turgitol® 15-S-9. The surfactant may be supplied as a powder, a liquid, or a gel. In certain embodiments, the extraction component comprises a solid phase sorbent. In certain embodiments, the solid phase sorbent comprises C18 silica. In certain embodiments, the solid phase sorbent comprises GracePure™ SPE C 18-Max, Phenomenex Strata PAH 8B-S 130-WCH, or both. In certain embodiments, the solid phase sorbent is contained in a column. In certain embodiments, the PAH is removed from the column with an organic solvent. In certain embodiments, the solid phase sorbent is contained in a filter disk, for example, a 3M Empore™ #2215-C18 extraction disk. In certain embodiments, the PAH is eluted from the column with an organic solvent.

Certain Exemplary Embodiments

Reaction scheme of colorimetric PAH detection. As depicted in FIG. 2, certain method embodiments can be illustrated as a series of chemical reactions. In one exemplary embodiment, naphthalene may be detected through subsequent reactions allowing NDO activity (i), NAD(P)H deactivator activity (ii), NahB activity (iii), and MPMS activity (iv). Alternatively, a diaphorase may be substituted for MPMS to engender a chemical transformation (v). The electron acceptors (tetrazolium salt and resazurin) may be substituted with one another in this example.

Figure 4:
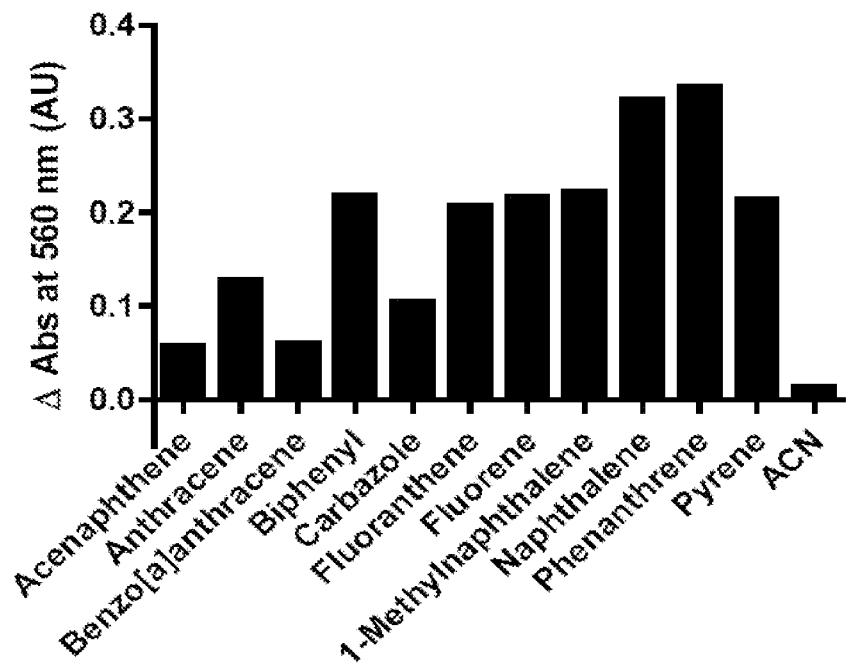
FIG. 4: Detection of various PAH using a microplate reader to measure absorbance. A series of first reaction solutions comprising NDO (an exemplary PAH dioxygenase), NADH cofactor, and 10 ppm of a variety of PAH species in separate wells of a microtiter plate (one PAH species per well) were incubated at room temperature for 30 minutes. Then Thiazoyl Blue Tetrazolium Bromide (an exemplary electron acceptor), MPMS (an exemplary electron carrier), and NahB (an exemplary dihydroxy-dihydro PAH dehydrogenase) were added to each well, forming second reaction solutions and a detectable colorimetric signal was generated. The signals at 560 nm were measured after 5 minutes incubation. A reaction solution comprising the acetonitrile diluent but no PAH, ACN in FIG. 4, was used as a negative control.

Oxaloacetate induces the depletion of NADH in the presence of $E.$ $coli$ lysate containing NDO. As depicted in FIG. 4, NDO consumed NADH at a faster rate in the presence of naphthalene. A 100 mM oxaloacetate stock solution was prepared by dissolving oxaloacetic acid in ddH$_2$O, adjusting pH to 7.0 with sodium hydroxide aqueous solution, and adjusting final volume to match desired concentration. 2497 µL of 50 mM TrisCl pH 7.5, 5% glycerol, and 2 mM DTT was mixed with 200 µL of 3 mM NADH dissolved in 20 mM sodium phosphate pH 7.0 and 3 µL of naphthalene dissolved at 20.5 mg/mL in DMF solvent to create a reaction mix "naphthalene". A 0 ppm naphthalene reaction mix "blank" was also prepared in a similar manner, with only DMF solvent added instead of naphthalene. A separate reaction mix "oxaloacetate" was prepared by mixing 2464 µL of 50 mM TrisCl pH 7.5, 5% glycerol, and 2 mM DTT with 33 µL of 100 mM oxaloacetate, 200 µL of 3 mM NADH and 3 µL of DMF solvent. 270 µL of each reaction mix was added to 30 µL of $E.$ $coli$ lysate containing NDO in a Costar 2592 microtiter plate. The absorbance of this mixture was evaluated at 340 nm at multiple time points over 50 minutes using a BioTek Synergy 2 plate reader at room temperature.

Figures 5A, 5B:
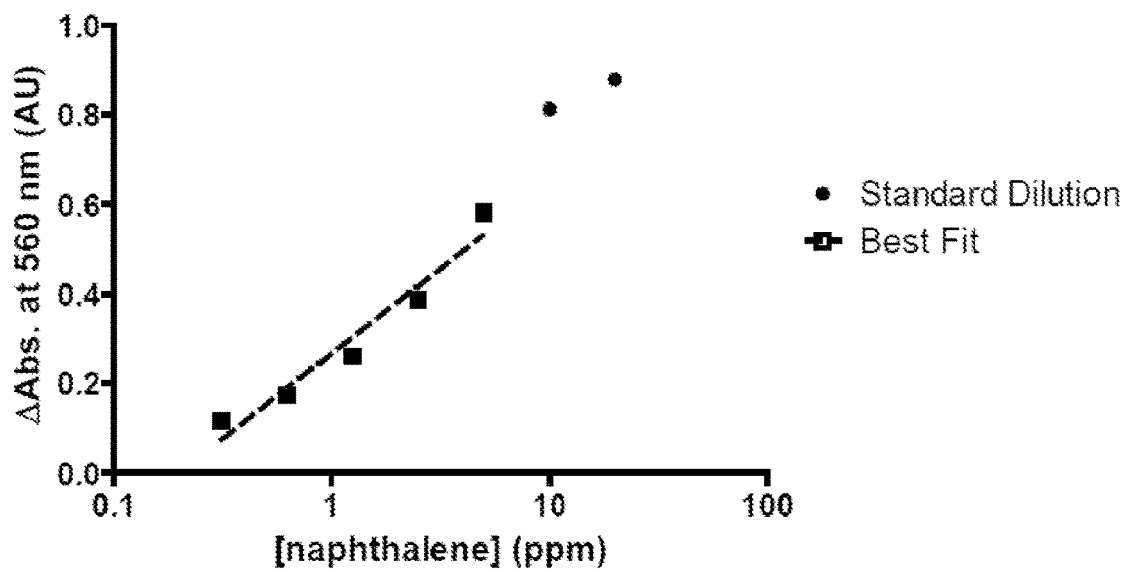
FIGS. 5A and 5B.

Colorimetric detection of PAH in organic solvent. As depicted in FIG. 5, a variety of PAH can be detected utilizing the disclosed methods. Illustrative samples comprising 10 µL of various PAH dissolved at a concentration of 0.2 mg/mL in acetonitrile were added to different wells of a clear-bottom 96-well microtiter plate (Grenier 675161). $E.$ $coli$ lysate containing NDO diluted 1:15.5 in 50 mM sodium phosphate pH 7.0, was added as a 155 µL volume and mixed. 15 µL of a 3 mM NADH solution in 20 mM phosphate pH 7.0 was added. Mixture was incubated at room temperature for 30 minutes. To initiate the second step, 10 µL of reagent mix was added (1 mM Thiazoyl Blue Tetrazolium Bromide, 0.05 mg/mL MPMS in ddH$_2$O). 10 µL of $E.$ coli lysate containing NahB was added. Color change and absorbance were monitored at 560 nm after a 5 minute interval at room temperature using a BioTek Synergy 2 plate reader. The change in absorbance at 560 nm "ΔAbs" was graphed to determine the presence or absence of PAH in the illustrative samples.

Figure 6:
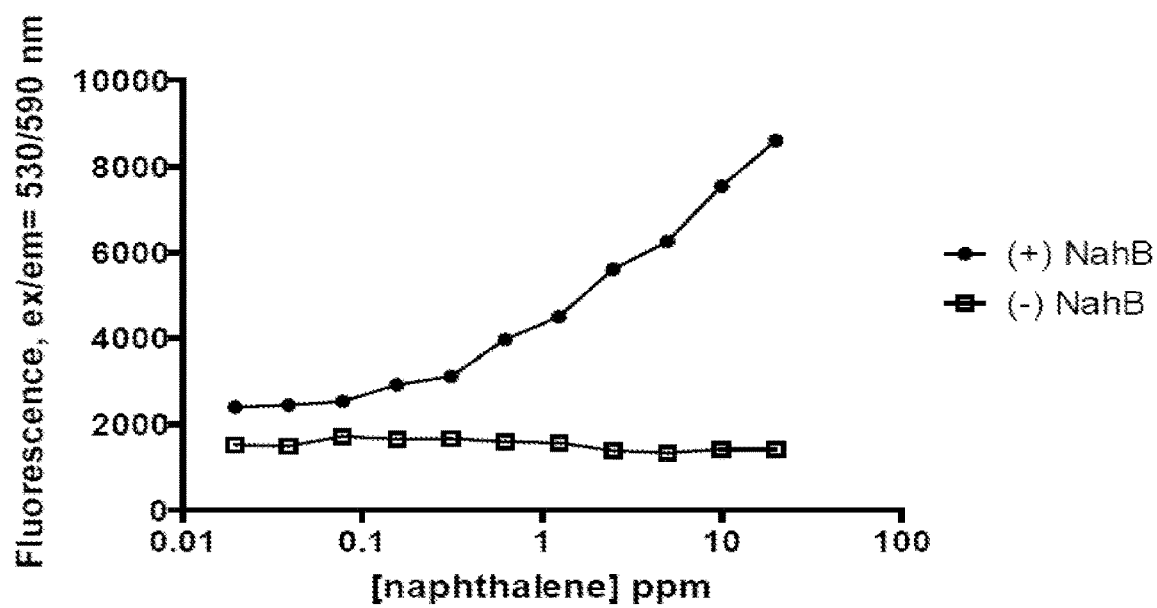
FIG. 6: Detection of fluorescent signals generated using a naphthalene standard. A series of first reaction solutions comprising NDO, NADH, and a serial dilution of a naphthalene standard were prepared in separate wells of a microtiter plate. The plate was incubated for 30 minutes at RT. Next resazurin and diaphorase are added to each well. NahB was also added to some, but not all of these reaction solutions. The results, shown in FIG. 6, demonstrate that when NahB is included in the second reaction solutions, a detectable fluorescent signal (measured at 590 nm) is generated in a naphthalene concentration dependent manner, while little to no signal is detected in reaction solutions that did not comprise NahB.

Colorimetric detection of PAH in petroleum tar and sand. FIG. 6 depicts the result of detecting PAH in a tar sample surfactant extract. 50 mL of a 10% Triton X-114 solution in milliQ water was added to 50 g of a petroleum tar and sand in a glass beaker with a magnetic stirbar. The mixture was stirred overnight at room temperature. Approximately 22 g of the slurry was transferred to two 50 mL conical tubes. A stock solution of 10 mg/mL naphthalene in acetonitrile was added to one tube as a 100 ppm spike, and an equal volume of acetonitrile was added to the non-blank. Following rigorous vortexing, the tubes were centrifuged 15 minutes at 2000 rpm at 8° C. Supernatants were pipetted into fresh 50 mL conical tubes. Supernatants were heated to 60° C. for 2 hours to induce phase separation, and centrifuged again for 5 minutes at 3500 rpm at room temperature. The surfactant phase was isolated as the middle liquid phase, as a solid precipitate formed as the bottom-most phase. A naphthalene standard serial dilution was conducted with 5 μL naphthalene standard in acetonitrile added to each well to achieve a 20 ppm to 0.1 ppm calibration curve in a 96-well Costar® 2592 plate. 155 4 of 0.1% Triton X-114 was added to standard wells. Samples were diluted 500-fold in 0.1% Triton X-114. 155 μL of diluted aqueous surfactant sample was added to a 96-well clear bottom plate. Addition of 5 μL acetonitrile followed to match the naphthalene standard dilution. 5 μL of 1 M sodium phosphate pH 7.0 followed to each sample well. 10 μL of an E. coli lysate comprising NDO, and 10 μL of 3 mM NADH were added to form a first reaction solution. The plate was incubated for 30 minutes at room temperature. 100 mM oxaloacetate stock was prepared by dissolving oxaloacetic acid in ddH$_2$O, adjusting pH to 7.0 with sodium hydroxide aqueous solution, and adjusting final volume to match desired concentration. 10 μL 100 mM oxaloacetate was added to the wells and the plate was incubated for an additional 30 minutes at room temperature. 5 μL of 4 mM Thiazoyl Blue Tetrazolium Bromide with 0.1 mg/mL MPMS was added to each well and mixed. 10 μL of E. coli lysate comprising NahB preparation was added to all wells except blanks, forming second reaction solutions. Color change and absorbance at 560 nm were monitored over a 15 minute incubation period at room temperature using a BioTek Synergy 2 plate reader. The change in absorbance at 560 nm "ΔAbs" was graphed. Samples were compared to naphthalene serial dilution to estimate PAH levels as naphthalene equivalence (NE) units.

Figures 7A, 7B:
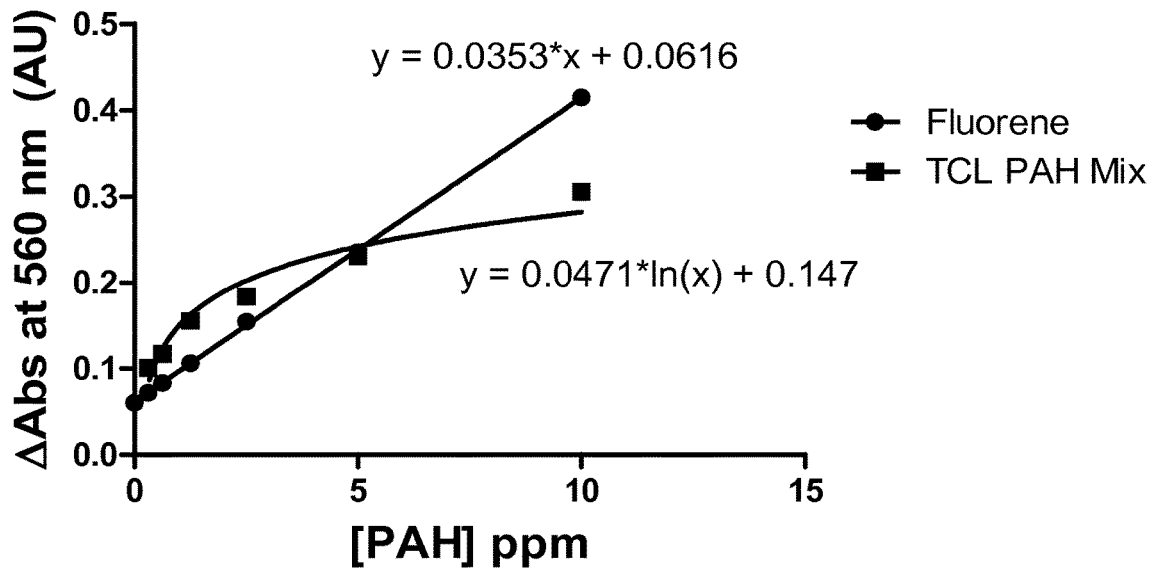
FIGS. 7A and 7B: Detection of PAH in extracted samples.

Fluorescent detection of PAH in organic solvent. As depicted in FIG. 7. A serial two-fold dilution of naphthalene was prepared from 800 ppm to 1.6 ppm in acetonitrile. 5 μL of this naphthalene serial dilution was added to the wells of a Costar 2592 microtiter plate. E. coli lysate, containing NDO diluted 1:25 in 50 mM sodium phosphate pH 7.0, was added to each well in a 185 μL volume and mixed. 10 μL of a 3 mM NADH solution in 20 mM phosphate pH 7.0 was added. The plate was then incubated at room temperature for 30 minutes. 10 μL of reagent mix (400 μM resazurin, 0.7 U/mL diaphorase in 50 mM sodium phosphate pH 7.0) was then added and mixed in the wells. Next, 10 μL of E. coli lysate containing NahB or 10 μL of 50 mM sodium phosphate pH 7.0 as a no NahB control were added to the wells (depicted in FIG. 7 as (+) NahB and (−) NahB, respectively). Fluorescence was monitored at $\lambda_{ex}$=530 nm (bandpass=25 nm), and $\lambda_{ex}$=590 nm (bandpass=35 nm) with mirror set to top 50%, read height=7 mm, 10 measurements per data point and gain=40 after 20 minutes at room temperature using a BioTek Synergy 2 plate reader.

Preparation and extraction of aqueous PAH spikes. Two samples of 1 L of ddH$_2$O in glass jars, were spiked with 1 mL of 1000 ppm flourene (in acetonitrile) or 356.8 μL of TCL PAH mix in acetonitrile (Sigma #49156, total stock PAH content of 2800 ppm), vigorously mixed manually for 1 minute, then transferred to a 1000 mL separatory funnel. GracePure SPE C18-Max 1000 mg cartridges were prepared using a vacuum manifold. Each cartridge was washed with the following and let drain after each was: four 10 mL aliquots of dichloromethane, four 10 mL aliquots of methanol and two 10 mL aliquots of ddH$_2$O, the second time keeping the cartridge wet. Sample was applied to each cartridge from the separatory funnel and passed through the column with vacuum assistance. The cartridge was then washed with 10 mL reagent water and dried with the vacuum for 10 minutes. The cartridges were then removed from the extraction train and placed on a vacuum manifold with sample collection tubes for elution. The samples were eluted from the cartridge with two 5 mL aliquots of dichloromethane. Each eluate was passed through a "drying column" consisting of a chromatographic column packed with 1 inch of anhydrous sodium sulfate. The dried eluates were evaporated with a stream of nitrogen to a volume of 1.0 mL. 3 mL of acetonitrile was added to each eluate and these solutions were evaporated down to a volume of 0.5 mL. This was repeated to remove the majority of dichloromethane remaining in the sample. Samples were diluted serially into acetonitrile and subsequently assayed.

Enzymatic detection of PAH extractions. As depicted in FIG. 8, PAH extracted from an aqueous sample may be detected using certain disclosed methods. All reactions were in a final volume of 300 μL in separate wells of a microtiter plate. 100 mM oxaloacetate stock was prepared by dissolving oxaloacetic acid in ddH$_2$O, adjusting the pH to 7.0 with sodium hydroxide aqueous solution, and adjusting the final volume to match desired concentration. A PAH standard was prepared as a serial two-fold dilution from 300-0 ppm in acetonitrile from either a 1000 ppm fluorene stock or a 2800 ppm TCL PAH mix stock (Sigma #49156) in acetonitrile. Initial reactions in each well included 200 μL 50 mM TrisCl pH 7.5, 10 μL each of E. coli lysate containing NDO, 10 μL PAH standard or sample and 10 μL 4 mM NADH prepared in 10 mM TrisCl pH 8.5. Reactions were mixed and incubated for 30 minutes at room temperature. After incubation, 10 μL 100 mM oxaloacetate was added to each well and incubated 5 additional minutes at room temperature. 30 μL of a 1 mM Thiazoyl Blue Tetrazolium Bromide with 0.025 mg/mL MPMS mixture were added to the reaction. An initial absorbance was taken at 560 nm using a BioTek Synergy 2 plate reader at room temperature followed by the addition of 30 μL of 6 μM purified NahB (diluted into 50 mM TrisCl pH 7.5 from freezer stock). Final absorbance at 560 nm was taken after 20 minutes. The change in absorbance "ΔAbs" at 560 nm was graphed against the PAH concentration in ppm to determine the concentration of PAH in the extract samples.

Although the disclosed teachings have been described with reference to various applications, methods, and compositions, it will be appreciated that various changes and modifications may be made without departing from the teachings herein. The foregoing examples are provided to better illustrate the present teachings and are not intended to limit the scope of the teachings herein. Furthermore, various presently unforeseen or unanticipated alternatives, modifications, variations or improvements therein may be subsequently made by those skilled in the art which are also intended to be encompassed by the following claims. Certain aspects of the present teachings may be further understood in light of the following claims.

What is claimed is:

1. A method for detecting the presence of polyaromatic hydrocarbon (PAH) in a sample, comprising:
   combining a sample with at least one PAH dioxygenase and at least one NAD(P)H cofactor to farm a first reaction solution;

incubating the first reaction solution under conditions suitable for forming dihydroxydihydro PAH and NAD(P)+;

adding at least one electron acceptor, at least one electron carrier, and at least one dihydroxy-dihydro PAH dehydrogenase to form a second reaction solution;

incubating the second reaction solution under conditions suitable for generating a detectable signal; and measuring the detectable signal, thereby detecting the presence of PAH in the sample.

2. The method of claim 1, wherein the at least one PAH dioxygenase comprises a recombinant cell lysate comprising naphthalene-1,2-dioxygenase from *Pseudomonas putida*.

3. The method of claim 2, wherein the cell lysate further comprises at least one NAD(P)H deactivator.

4. The method of claim 1, wherein the at least one dihydroxy-dihydro PAH dehydrogenase comprises 1,2-dihydroxy-1,2-dihydronapthalene dehydrogenase from *Pseudomonas putida*.

5. The method of claim 1, wherein the at least one electron acceptor comprises resazurin and the at least one electron carrier comprises at least one diaphorase.

6. The method of claim 5, wherein the at least one diaphorase comprises *Clostridium kluyveri* diaphorase.

7. The method of claim 1, wherein the at least one electron acceptor comprises at least one tetrazolium salt and the at least one electron carrier comprises at least one derivative of phenazinium methyl sulfate.

8. The method of claim 6, wherein the at least one derivative of phenazinium methyl sulfate comprises at least one of 1-methoxy-5-methylphenazinium methyl sulfate or phenazine methosulfate.

9. The method of claim 7, wherein the at least one tetrazolium salt comprises thiazoyl blue tetrazolium bromide.

\* \* \* \* \*